United States Patent [19]

Mott et al.

[11] Patent Number: 4,854,173
[45] Date of Patent: Aug. 8, 1989

[54] MEASUREMENT OF INTERGRANULAR ATTACK IN STAINLESS STEEL USING ULTRASONIC ENERGY

[75] Inventors: Gerry Mott, Pittsburgh; Mustan Attaar; Rick D. Rishel, both of Monroeville, all of Pa.

[73] Assignee: The United States of America as represented by the United States Department of Energy, Washington, D.C.

[21] Appl. No.: 163,360

[22] Filed: Mar. 2, 1988

[51] Int. Cl.[4] ........................................... G01N 29/04
[52] U.S. Cl. ....................................................... 73/600
[58] Field of Search ................... 73/600, 599, 592, 586

[56] References Cited

U.S. PATENT DOCUMENTS

| | | |
|---|---|---|
| 3,939,404 | 2/1976 | Tait . |
| 3,946,600 | 3/1976 | Rettig et al. . |
| 4,184,373 | 1/1980 | Evans et al. . |
| 4,393,711 | 7/1983 | Lapides ................................. 73/592 |
| 4,428,236 | 1/1984 | Votava et al. . |
| 4,449,408 | 5/1984 | Brooks et al. . |
| 4,449,411 | 5/1984 | Suhr et al. . |
| 4,450,405 | 5/1984 | Howard . |
| 4,461,995 | 7/1984 | Harris . |
| 4,466,287 | 8/1984 | Repplinger et al. . |
| 4,522,064 | 1/1985 | McMillan ............................... 73/600 |
| 4,596,142 | 6/1986 | Poole et al. ........................... 73/579 |
| 4,640,131 | 2/1987 | Kroning et al. ....................... 73/600 |
| 4,685,334 | 8/1987 | Latimer ................................. 73/599 |

OTHER PUBLICATIONS

G. J. Curtis, "The Use of Surface Elastic Waves in Examining Surface Mechanical Properties", in *Ultrasonic Testing*, (N.Y., J. Wiley & Sons, 1982), J. Szilard, ed., pp. 317-319.

Primary Examiner—John Chapman
Attorney, Agent, or Firm—Allen F. Westerdahl; Judson R. Hightower

[57] ABSTRACT

Ultrasonic test methods are used to measure the depth of intergranular attack (IGA) in a stainless steel specimen. The ultrasonic test methods include a pitch-catch surface wave technique and a through-wall pulse-echo technique. When used in combination, these techniques can establish the extent of IGA on both the front and back surfaces of a stainless steel specimen from measurements made on only one surface.

8 Claims, 4 Drawing Sheets

MEASUREMENT OF INTERGRANULAR ATTACK IN STAINLESS STEEL USING ULTRASONIC ENERGY

FIELD OF THE INVENTION

The present invention relates generally to non-destructive testing of materials, and more specifically to non-destructive measurement of intergranular attack in stainless steel.

BACKGROUND OF THE INVENTION

Volumetric grain boundary, or intergranular attack (IGA) is a type of stress corrosion in metals that may result in cracking under a combination of high tensile stresses and corrosive environments.

In stainless steel, sensitization (weakening of bonds) results from heating nonstabilized stainless steel, causing precipitation of chromium-rich carbides along grain boundaries. These grain boundaries are thus susceptible to corrosion under certain operating conditions. In this type of corrosion, IGA initiates at a free surface and continues propagating as a plane front into the material so that a layer of IGA, whose severity is more or less uniform over a plane but which varies with depth, is formed. The cohesion of grain boundaries in the region of IGA in the vicinity of the surface may be severely weakened to the extent that little cohesive strength remains. For a surface in this state, thermal stresses associated with welding can be sufficiently large to pull grains apart, causing crack initiation sites to form. For stainless steel, tensile stresses that may cause cracking include residual stresses due to welding or fabrication, and other thermally-induced stresses. Environments that cause stress-corrosion cracking include aqueous solutions of chlorides, flourides, hydroxide ions, or dissolved oxygen. Stress-corrosion cracking may also occur in high-temperature water or boiling water nuclear power plants.

Although various methods exist for controlling sensitization, it is frequently difficult to control or predict. Sensitized steel, during use, can be exposed to conditions that promote IGA. Knowledge of the presence and extent of IGA, therefore, would be beneficial to alleviate potential problems.

Several systems for detecting flaws in metals using acoustic waves and/or eddy currents are known in the art. For example, U.S. Pat. No. 4,184,373 to Evans generally discloses a system for ultrasonically evaluating adhesive bonds between metal surfaces by comparing various echo amplitudes. Rettig U.S. Pat. No. 3,946,600 and Votava U.S. Pat. No. 4,428,236 disclose measurement of acoustic pulses emitted by the corrosion process in metals to predict failure and to locate a corroded area. Tait U.S. Pat. No. 3,939,404 and Howard U.S. Pat. No. 4,450,405 are representative of patents that generally show the use of eddy current testing to detect defects in metals.

SUMMARY OF THE INVENTION

The present inventive approach to testing for and measurement of intergranular attack relies on the application of ultrasonic test principles. The ultrasonic techniques described herein are used to measure IGA on both the near and far (remote) surfaces of stainless steel; for example, stainless steel plates and pipes.

The ultrasonic techniques mentioned above encompass two test procedures. The first procedure utilizes two ultrasonic tranducers as transmitter and receiver in a pitch-catch configuration for interface wave testing of the near surface of a test specimen. The second procedure utilizes a single transducer as both transmitter and receiver in reverberation echo testing of the test specimen.

To measure the depth of IGA using the present inventive system, ultrasonic wave testing of the near surface of the specimen is first carried out using the pitch-catch configuration. The remote surface (in a pipe, the inner wall surface) is then tested by finding the total reverberation echo decibel ratio for both near and remote surfaces using the single ultrasonic transducer configuration. The near surface IGA measurement derived using the pitch-catch configuration is used to find the near surface contribution to the total reverberation echo decibel ratio for both surfaces, from which the near surface contribution is then subtracted to determine the remote surface contribution. Working backward, the remote surface IGA depth is then found from this remote surface contribution to the total reverberation echo decibel ratio.

DETAILED DESCRIPTION OF THE INVENTION

An example of the process according to the present invention for measuring intergranular attack (IGA) was carried out using Type 304 stainless steel in plate form utilizing ultrasonic principles. The ultrasonic means of measuring IGA consists of two approaches. The first approach uses an interface wave specifically chosen for its ability to detect variations in the acoustic properties of only a thin layer of material in the surface where the ultrasound wave enters the test piece. This wave dissipates with depth below the surface, and its amplitude normally (i.e., in the absence of IGA) falls to 1/e of its surface value at a depth of about one wavelength.

Figure 1:
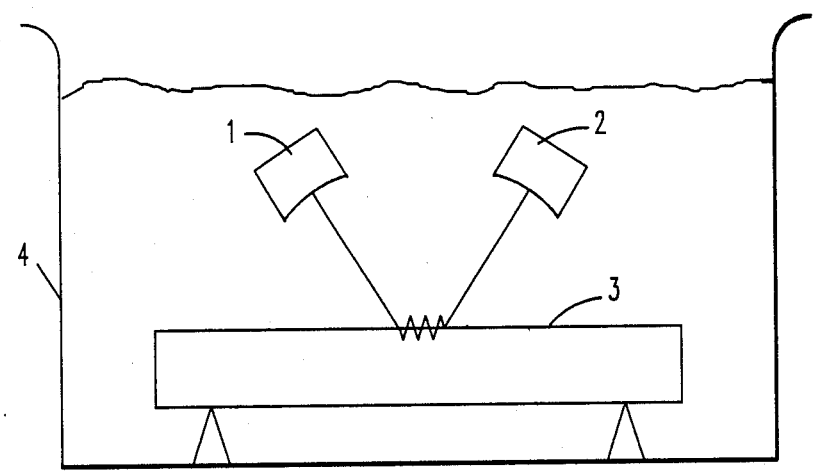
FIG. 1 is a side view of the interface wave test system of the invention.

As shown in FIG. 1, the interface wave test is carried out using two ultrasonic transducers in a transmit-receive, or "pitch-catch", configuration. The transmitter and receiver pair (each for example, 2.25 MHz, 1.27 cm [0.5 inch]diameter) is set into a holder (not shown) to ensure that each interface wave is generated and detected at the correct angle. The holder, transmitter 1, and receiver 2 are then immersed in water in tank 4, with transmitter 1 and receiver 2 arranged to ensure that approximately a 0.64 cm (0.25 inch) segment of surface of the stainless steel plate 3 under test is traversed by the interface wave in its path from transmitter 1 to receiver 2.

An actual interface wave test procedure was carried out as follows: A stainless steel specimen in plate form 3 is first chosen to be a reference specimen known to have substantially no IGA. The system shown in FIG. 1 is used to measure the attenuation of an interface ultrasonic wave that traverses the reference specimen as described in the preceeding paragraph. The reference specimen is then replaced by a test specimen also in plate form, and the test is repeated. A decibel ratio of the reflected reference signal amplitude to the reflected test signal amplitude is then established. This ratio, which is termed the "first surface interface wave attenuation decibel ratio", can be correlated with ultrasonic attenuation by normalization or any of a number of known mathematical methods and, in turn, with an estimated IGA depth; as explained below.

Calibration data was obtained from destructive test measurements of actual IGA depth and its related interface wave attenuation (change in attenuation between reference and test plate specimens), directly relating the two parameters. This experimentally determined data is shown graphically in FIG. 2. The linear relationship shows that, given a measured interface wave attenuation decibel ratio, IGA depth for a test plate specimen may be estimated from a trace Y, expressing the data obtained from the test.

Figure 3:
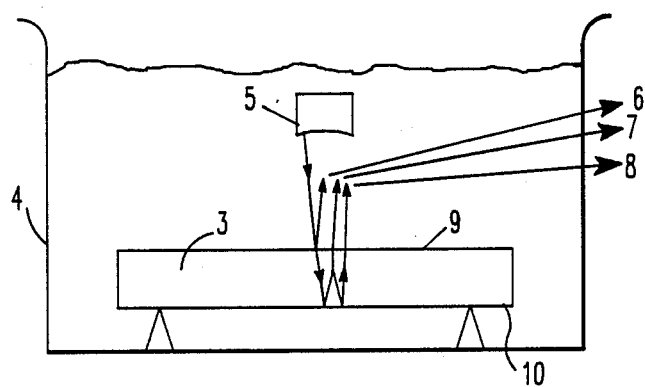
FIG. 3 is a side view of the reverberation echo test system of the invention.
Figure 4:
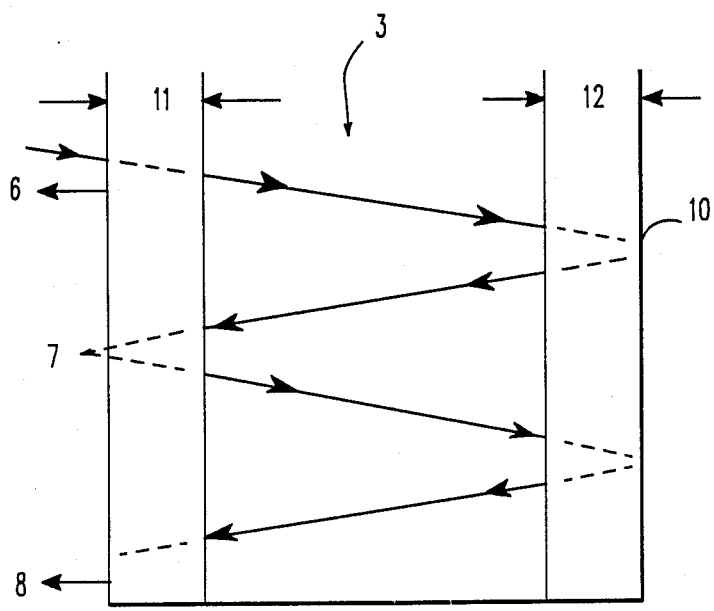
FIG. 4 is a schematic showing the passage of ultrasonic waves through a test specimen, and the echoes of the ultrasonic waves from each specimen surface, according to the reverberation echo test procedure of the invention.

The second ultrasonic approach, shown in FIG. 3, uses a longitudinal wave transducer 5 (for example having a diameter of 1.27 cm [0.5 inch]) immersed in tank 4 directly above specimen 3, in this example a plate, and in place of the transmitter-receiver pair used for the interface wave test. In the preferred embodiment, transducer 5 is oriented such that its ultrasonic output strikes the near, or first, surface of specimen 3 at essentially normal incidence to the surface; a two-transducer transmit-receive system could also be used, enabling the wave to be transmitted and received at other than normal incidence. A pulse-echo method is used. FIG. 3 identifies the first three echoes received by transducer 5. Of course, more echoes will result, but only three are shown for simplicity. Reference numeral 6 represents the portion of the transmitted beam that echoes from first or near surface 9 of the sample, reference numeral 7 identifies the first echo from the remote, or second, surface 10, and reference numeral 8 identifies the second echo from second surface 10 (after having internally reflected at first surface 9). The amplitude of each echo is related to the average acoustic properties of the specimen, and is therefore dependent on variations of acoustic properties due to scattering losses in the IGA layers at its first and second surfaces 9 and 10, respectively. Such variations are shown in the calculations below, which have been derived from known plane wave theory.

amplitude of initial near surface echo:

$RS_1$ amplitude of transmissive beam:

$S'_1 e^{-\alpha d_1} \sqrt{1 - R^2}$ amplitude of first remote surface echo:

$S'_1 e^{-\alpha(d_1 + 2d_2)} \sqrt{1 - R^2} \, RS_2$ amplitude of first received transmissive beam:

$(1 - R^2) S_1'^2 RS_2 e^{-2\alpha(d_1 + d_2)}$ amplitude of first near surface internally reflected beam:

$S_1' R^2 S_1 S_2 e^{-\alpha(3d_1 + 2d_2)} \sqrt{1 - R^2}$ amplitude of second remote surface echo:

$S_1' R^3 S_1 S_2^2 e^{-\alpha(3d_1 + 4d_2)} \sqrt{1 - R^2}$ amplitude of second received transmissive beam:

$(1 - R^2) S_1'^2 R^3 S_1 S_2^2 e^{-4\alpha(d_1 + d_2)}$ where:
$S_1$, $S_1'$, $S_2$, and $S_2'$ are back- and forward-scattering losses for first and second IGA layers of depths $d_1$ and $d_2$ (represented by reference numerals 11 and 12, respectively);
$\alpha$ is IGA layer attenuation coefficient; and
R is water/steel reflection coefficient.

The calculations may be continued as long as is necessary or desired; the decibel ratio of the amplitudes of the second-to-first surface echo returns is then calculated to be $-20 [\log_{10} (e^{-2\alpha d_1} RS_1) + \log_{10} (e^{-2\alpha d_2} RS_2)]$.

This result shows that the total measured decibel ratio is the sum of two independent contributions—one from first surface 9 and one from the second surface 10. The depth of IGA on the second surface 10 (contained in the second term) can be inferred from measurements made on only first surface 9 whenever the first term can be quantified, as set forth below.

Figure 2:
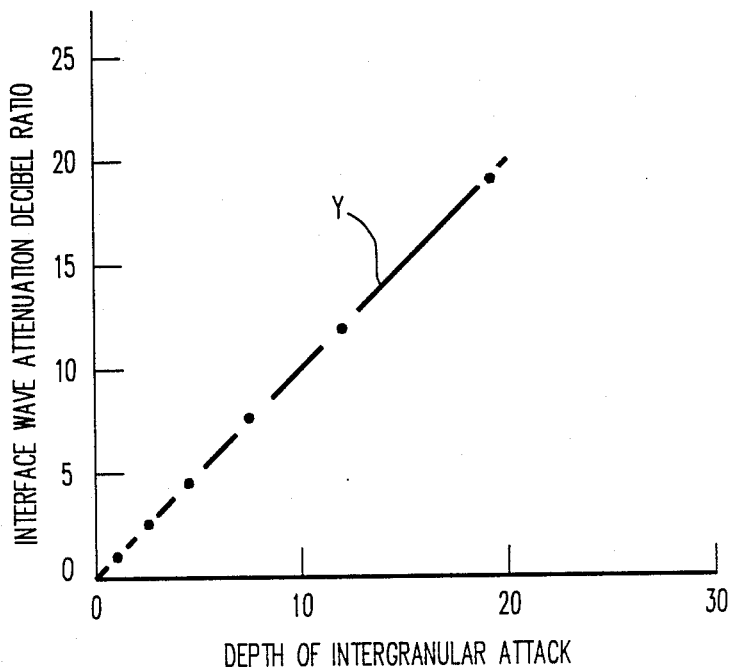
FIG. 2 is a plot of interface wave attenuation versus depth of intergranular attack.

The method, then, for estimating the depth of a layer of IGA in second surface 10 is to first measure the interface wave attenuation decibel ratio for first surface 9, find its value on the ordinate of the graph shown in FIG. 2, and then obtain from the trace Y the depth of IGA in first surface 9. The total reverberation echo decibel ratio of second surface 10 to first surface 9 is next measured using the single transducer system outlined above. The first surface interface wave attenuation decibel ratio is then converted to a reverberation echo decibel ratio using the graph shown in FIG. 6. This graph represents a plot of reverberation echo decibel ratio to interface wave attenuation decibel ratio that is derived empirically. The value thus obtained represents the first surface contribution to the total reverberation echo decibel ratio found experimentally.

Subtracting the first surface contribution from the total reverberation echo decibel ratio (graphically from FIG. 6 or otherwise) given the contribution from second surface 10. By consulting the plot in FIG. 6 one more time, the second surface interface wave decibel ratio may be estimated from the second surface contribution to the total reverberation echo decibel ratio. Turning finally back to the graph shown in FIG. 2, the depth of IGA in second surface 10 may be estimated from this value for second surface interface wave attenuation decibel ratio.

Figure 5:
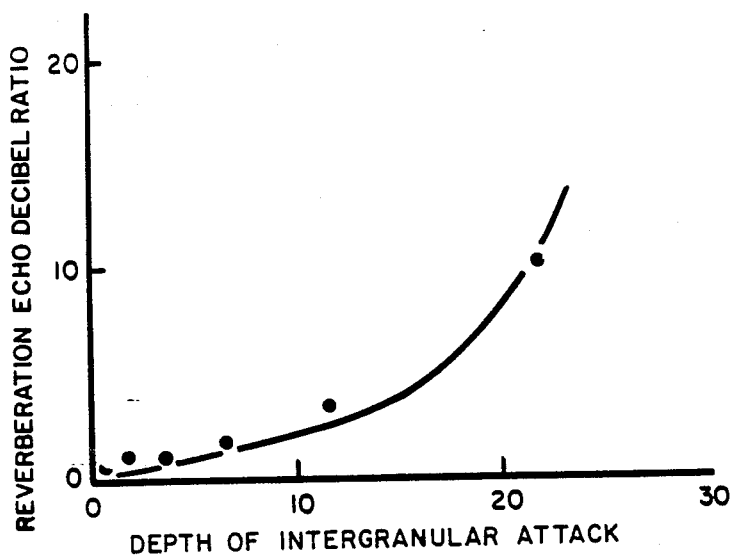
FIG. 5 is a plot of reverberation echo decibel ratio versus depth of intergranular attack.
Figure 6:
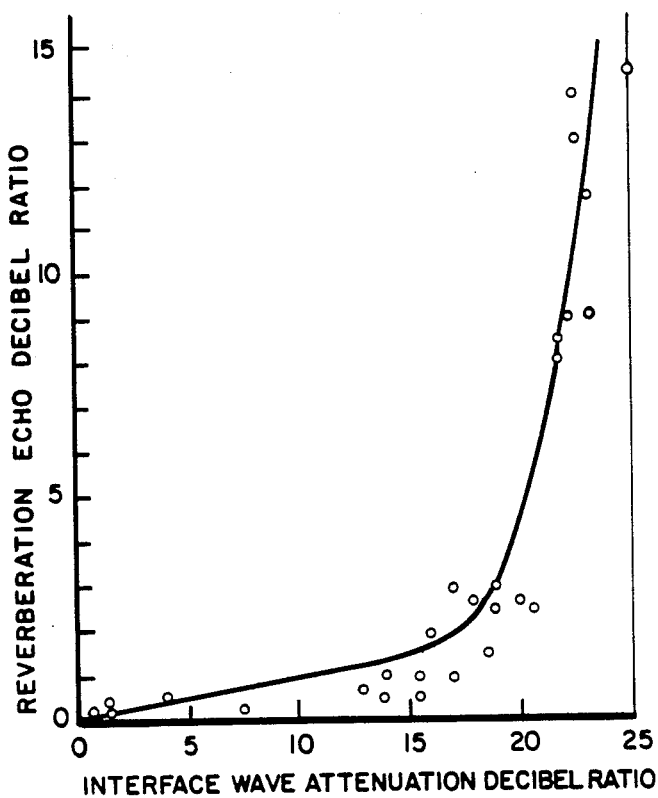
FIG. 6 is a plot of reverberation echo decibel ratio versus interface wave attenuation.

Alternatively, the second surface IGA may be found using the graphical data of FIG. 5 rather than that of FIG. 6. By consulting FIG. 5, the total depth of IGA for the two surfaces 9 and 10 ($d_1+d_2$) may be estimated from the experimentally-determined total reverberation echo decibel ratio. The previously-derived value for $d_1$ may then be subtracted from the estimated sum, leaving $d_2$.

Eddy current techniques for confirming measurements of first-surface depth of intergranular attack may be used to verify the ultrasonic interface wave test results.

Figure 7:
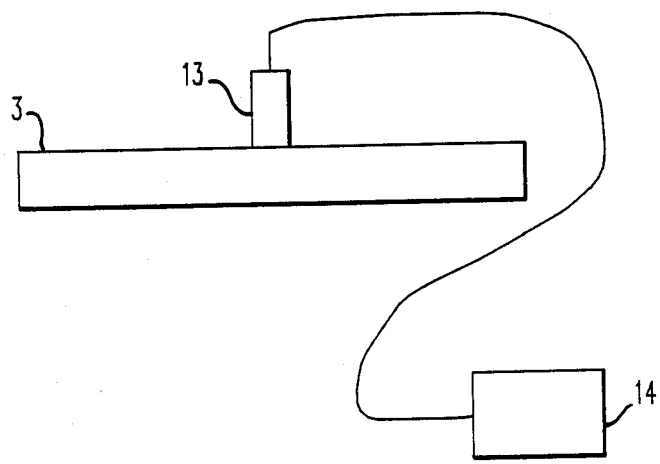
FIG. 7 is a side view of an optional eddy current test procedure.

FIG. 7 illustrates a known eddy current approach which uses a standard off-the-shelf probe 13 at a frequency of 100 kHz in a surface-riding technique. The approach uses a standard eddy current instrument 14 connected with the above-described probes, which is laid flat on the surface being interrogated. A thin layer of Teflon tape (not shown) may be added as a wear surface for the probe.

One of ordinary skill in the art will readily realize that specific modifications in the invention may be made. For example, the several derivations of intermediate and final value necessary to determining depth of IGA may be carried out in ways other than graphically, e.g., in a software program that implements the graphic relationships by other than direct plotting. Furthermore, the various decibel ratios could be derived from comparisons between measured values and various reference values, including but not limited to previous test values, transmitted amplitude values, or any other values from which a normalized comparison could be made. The various graphic relationships, of course, could be modified to comport with the different normalized comparisons.

Various other modifications of the equipment and techniques discussed above will become apparent to those skilled in the art. All such variations that basically rely on the teachings through which the invention has advanced the art are properly considered within the spirit and scope of the invention.

What is claimed is:

1. A method for determining depth of intergranular attach at the surfaces, in a stainless steel specimen having at least two spaced-apart surfaces, comprising the steps of:
    transmitting a first acoustic test wave toward a first surface of a stainless steel test specimen and receiving a reflection of said first test wave from said first surface;
    measuring the amplitude of said reflected first test wave;
    establishing an interface wave attenuation decibel ration between a predetermined reference value, corresponding to a value of said reflected first test wave assuming no intergranular attack in said test specimen, and said amplitude of said reflected first test wave;
    empirically deriving a relationship between interface wave attentuation decibel ratio and depth of intergranular attach in the first surface of a stainless steel specimen corresponding in composition to said test specimen;
    deriving the depth of intergranular attach in said first surface said relationship between interface wave attenuation decibel ratio and depth of intergranular attack;
    transmitting a second acoustic test wave toward said test specimen and reflecting said second test wave from said test specimen as a plurality of beams, wherein one of said beams is from said first surface, and all other said beams are from a second surface;
    measuring the amplitude of a first received transmissive beam and a second received transmissive beam and deriving the ratio of the two said amplitudes of said beams to obtain a total reverberation echo decibel ratio resulting from both said surfaces;
    empirically deriving a relationship between reverberation echo decibel ratio and interface wave attenuation decibel ratio for a stainless steel specimen corresponding in composition to said test specimen;
    deriving a first surface echo decibel ratio from said relationship between reverbation echo decibel ratio and interface wave attenuation decibel ratio;
    subtracting said first surface echo decibel ratio from said total reverberation echo decibel ratio to obtain a second surface echo decibel ratio;
    deriving a second surface interface wave attenuation decibel ratio from said relationship between reverberation echo decibel ratio and interface wave attenuation decibel ratio; and
    deriving the depth of intergranular attach in said second surface from said relationship between interface wave attenuation decibel ratio and depth of intergranular attack.

2. A method for determining depth of intergranular attack in a stainless steel specimen having at least at least two spaced-apart surfaces as claimed in claim 1, wherein both said test waves are ultrasonic waves.

3. A method for determining depth of intergranular attack in a stainless steel specimen having at least two spaced-apart surfaces as claimed in claim 1, wherein said first test wave is transmitted and reflected using a system wherein a transmitter and a receiver are arranged such that said first test wave traverses a distance approximately 0.64 cm along said first surface.

4. A method for determining depth of intergranular attack in a stainless steel specimen having at least two spaced-apart surfaces as claimed in claim 1, wherein said predetermined reference value is established by transmitting a reference acoustic wave toward a reference surface of a reference stainless steel specimen corresponding in composition to said test specimen without intergranular attack, and measuring the amplitude of a reference reflected wave reflected from said reference surface.

5. A method for determining depth of intergranular attack in a stainless steel specimen having two spaced-apart surfaces as claimed in claim 1, wherein said second test wave is both transmitted and said echoes are received using a single transducer arranged to transmit said second test wave at substantially normal incidence to said first surface.

6. A method for determining depth of intergranular attack in a stainless steel specimen having at least two spaced-apart surfaces as claimed in claim 1, wherein said at least two spaced-apart surfaces are substantially parallel to each other.

7. A method for measuring depth of intergranular attach at the surfaces, in a stainless steel specimen having at least two spaced-apart surfaces, comprising the steps of:
    transmitting a first acoustic test wave toward a first surface of a stainless steel test specimen and receiving reflection of said first test wave from said first surface;

measuring the amplitude of said reflected first test wave;

establishing an interface wave attenuation decibel ratio between a predetermined reference value, corresponding to a value of said reflected first test wave assuming no intergranular attack in said test specimen, and said amplitude of said reflected first test wave; empirically deriving a relationship between interface wave attenuation decibel ratio and depth of intergranular attach in the first surface of a stainless steel specimen corresponding in composition to said test specimen;

deriving the depth of intergranular attack in said first surface from said relationship between interface wave attenuation decibel ratio and depth of intergranular attack;

transmitting a second acoustic test wave toward said test specimen and reflecting said second test wave from said test specimen as a plural of beams, wherein one of said beams is from said first surface, and all other said beams are from a second surface;

measuring the amplitude of a first received transmissive beam and a second received transmissive beam and deriving the ratio of the two said amplitudes of said beams to obtain a total reverberation each decibel ratio resulting from both said surfaces;

empirically deriving a relationship between reverberation echo decibel ratio and depth of intergranular attack in a stainless steel specimen corresponding in composition to said test specimen;

deriving the total depth of intergranular attack in said first and second surfaces from said relationship between reverberation echo decibel ratio and depth of intergranular attack; and deriving the depth of intergranular attack in said second surface by subtracting said first surface depth of intergranular attack from said total depth of intergranular attack.

8. A method for determining depth of intergranular attack at the surfaces in a stainless steel specimen having at least two spaced-apart surfaces, comprising the steps of:

transmitting a first ultrasonic test wave toward a first surface of a stainless steel test specimen and receiving a reflection of said first test wave from said first surface, wherein said first test wave is transmitted and reflected using a system wherein a transmitter and a receiver are arranged such that said first test wave traverses a distance approximately 0.64 cm along said first surface;

measuring the amplitude of said reflected first test wave;

establishing an interface wave attenuation decibel ratio between a predetermined reference value, corresponding to a value of said reflected first test wave assuming no intergranular attack in said test specimen, and said amplitude of said reflected first test wave, wherein said predetermined reference value is established by transmitting a reference ultrasonic wave toward a reference surface of a reference stainless steel specimen corresponding in composition to said test specimen without intergranular attack, and measuring the amplitude of a reference reflected wave reflected from said reference surface;

empirically deriving a relationship between interface wave attenuation decibel ratio and depth of intergranular attack in the first surface of a stainless steel specimen corresponding in composition to said test specimen;

deriving the depth of intergranular attack in said first surface from said relationship between interface wave attenuation decibel ratio and depth of intergranular attack;

transmitting a second acoustic test wave toward said test specimen and reflecting said second test wave from said test specimen as a plurality of beams, wherein one of said beams is from said first surface, and all other said beams are from a second surface which is substantially parallel to said first surface, and wherein said second test wave is both transmitted and said beams are received using a singe transducer arranged to transmit said second test wave at substantially normal incidence to said first surface;

measuring the amplitude of a first received transmissive beam and a second received transmissive beam and deriving the ratio of the two said amplitudes of said beams to obtain a total reverberation echo decibel ratio resulting from both said surfaces;

empirically deriving a relationship between reverberation echo decibel ratio and interface wave attenuation decibel ratio for a stainless steel specimen corresponding in composition to said test specimen;

deriving a first surface echo decibel ratio from said relationship between reverberation echo decibel ratio and interface wave attenuation decibel ratio;

subtracting said first surface echo decibel ratio from said total reverberation echo decibel ratio to obtain a second surface echo decibel ratio;

deriving a second surface interface wave attenuation decibel ratio from said relationship between reverberation echo decibel ratio and interface wave attenuation decibel ratio; and deriving the depth of intergranular attack in said second surface from said relationship between interface wave attenuation decibel ratio and depth of intergranular attack.

* * * * *